(12) United States Patent
Toyobuku et al.

(10) Patent No.: US 8,030,075 B2
(45) Date of Patent: Oct. 4, 2011

(54) CARRIER COMPOSITION FOR NUCLEIC ACID TRANSPORT

(75) Inventors: Hidekazu Toyobuku, Tokushima (JP); Hideo Miyao, Tokushima (JP); Masako Sato, Tokushima (JP); Kazuo Sekiguchi, Otsu (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 256 days.

(21) Appl. No.: 12/083,727

(22) PCT Filed: Oct. 17, 2006

(86) PCT No.: PCT/JP2006/320617
§ 371 (c)(1),
(2), (4) Date: Apr. 17, 2008

(87) PCT Pub. No.: WO2007/046356
PCT Pub. Date: Apr. 26, 2007

(65) Prior Publication Data
US 2009/0258923 A1 Oct. 15, 2009

(30) Foreign Application Priority Data
Oct. 18, 2005 (JP) .................. 2005-303497

(51) Int. Cl.
*C12N 15/88* (2006.01)
*C12N 15/11* (2006.01)
*A61K 9/127* (2006.01)

(52) U.S. Cl. ................. 435/458; 424/450; 514/44 A

(58) Field of Classification Search .............. 435/458; 424/450
See application file for complete search history.

(56) References Cited

U.S. PATENT DOCUMENTS

| 7,772,201 B2 | 8/2010 | Mixson |
| 2002/0187105 A1* | 12/2002 | Zou et al. ................. 424/45 |
| 2003/0096414 A1* | 5/2003 | Ciccarone et al. .......... 435/383 |
| 2003/0118635 A1* | 6/2003 | Dalsgaard et al. .......... 424/450 |
| 2005/0064595 A1* | 3/2005 | MacLachlan et al. ....... 435/458 |
| 2007/0087045 A1* | 4/2007 | Li et al. ................... 424/450 |

FOREIGN PATENT DOCUMENTS

| JP | 2005508394 A | 3/2005 |
| WO | 99/31132 A1 | 6/1999 |
| WO | 00/27795 A1 | 5/2000 |
| WO | WO 0234236 A2 * | 5/2002 |
| WO | 03040375 A1 | 5/2003 |
| WO | 2004/004758 A1 | 1/2004 |
| WO | 2004/033620 A2 | 4/2004 |
| WO | 2006/060182 A2 | 6/2006 |

OTHER PUBLICATIONS

Wen-Chi Tseng, et al, "Liposome-Based Gene Therapy", Pharmaceutical Science & Technology Today, Aug. 1998, pp. 206-213, vol. 1, No. 5.
Hassan Farhood, et al, "The Role of Dioleoyl Phosphatidylethanolamine in Cationic Liposome Mediated Gene Transfer", Biochimica Et Biophysica Acta, May 4, 1995, pp. 289-295, vol. 1235, No. 2.
Claudio Esposito, et al, "The Analysis of Serum Effects on Structure, Size and Toxicity of DDAB-DOPE and DC-CHOL-DOPE Lipoplexes Contributes to Explain Their Different Transfection Efficiency", Colloids and Surfaces B: Biointerfaces, Dec. 1, 2006, pp. 187-192, vol. 53, No. 2.
Office Action mailed Aug. 10, 2011, in corresponding Philippines Patent Application No. 12008500782 (in the name of Otsuka Pharmaceutical Co., Ltd.).

* cited by examiner

*Primary Examiner* — Brian Whiteman
(74) *Attorney, Agent, or Firm* — Sughrue Mion, PLLC

(57) ABSTRACT

An object of the present invention is to provide a nucleic acid delivery carrier composition of low toxicity and high safety, the carrier composition, when used to administer a nucleic acid such as an siRNA into an animal-derived cell or organism, being capable of delivering efficiently the nucleic acids into the cells while protecting it from being degraded; and a nucleic acid deliver composition containing the carrier and a nucleic acid. The carrier composition for delivery of a nucleic acid is prepared by mixing (A) a cationic lipid having a steroid skeleton with (B) a tertiary ammonium salt-type cationic lipid. The nucleic acid delivery composition is prepared by mixing the nucleic acid delivery carrier with a nucleic acid.

17 Claims, 5 Drawing Sheets
(2 of 5 Drawing Sheet(s) Filed in Color)

CARRIER COMPOSITION FOR NUCLEIC ACID TRANSPORT

TECHNICAL FIELD

The present invention relates to a low toxicity and high safety carrier composition for delivery of a nucleic acid, the carrier composition, when used to administer a nucleic acid such as an siRNA into an animal-derived cell or organism, being capable of delivering efficiently the nucleic acid into cells while protecting the nucleic acid from being degraded; and a nucleic acid delivery composition.

BACKGROUND ART

With the recent advances of biotechnology, various nucleic acids have been found to exhibit bioactive functions in cells. For example, siRNAs (small interfering RNAs) are known to cause degradation of mRNAs of target genes in cells and to thereby inhibit the expression of the target genes (RNA interference). Inhibition of target gene expression by RNA interference is useful for alleviating or treating disease symptoms caused by abnormal expression of specific genes or gene clusters, and therefore development of siRNAs as therapeutic agents is expected. However, in order to use nucleic acids such as siRNAs as therapeutic agents, it is important for such nucleic acids to exhibit their functions in target cells. For this purpose, it is indispensable that a technology to efficiently deliver nucleic acids into target cells be established.

Known technologies to deliver exogenous nucleic acid molecules or genes into cells include treatments of intractable diseases in humans using various viruses including retroviruses, adenoviruses, herpesviruses, etc. However, such treatments involve difficulties because of problems with infectivity, immunoreactivity, productivity and the like. Therefore, non-viral carriers that are free of problems caused by viruses and that can deliver nucleic acid molecules into cells are being developed.

For example, Patent Document 1 has reported a cationic lipid having a specific structure as a non-viral nucleic acid delivery carrier that promotes the delivery of nucleic acids such as siRNAs into cells. However, the cationic lipid reported in Patent Document 1 has a defect in that it exhibits toxicity when administered to cultured cells or organisms. Patent Document 2 discloses a carrier composition containing an amphiphilic compound and polycations as a relatively low-toxicity carrier that can deliver siRNAs into cells. However, the composition reported in Patent Document 2 also has a problem in its toxicity to cells when introducing a sufficient amount of siRNA thereto.

Against this prior art background, the development of a low-toxicity carrier composition for delivery of a nucleic acid that can efficiently deliver nucleic acids such as siRNA into cells is desired.

[Patent Document 1]
Japanese Unexamined Patent Application Publication No. 2002-529439
[Patent Document 2]
Japanese Unexamined Patent Application Publication No. 2005-508394

DISCLOSURE OF THE INVENTION

Problems to be Solved by the Invention

An object of the present invention is to solve the above problems of the prior art. Specifically, an object of the present invention is to provide a nucleic acid delivery carrier composition of low toxicity and high safety, the carrier composition, when used to administer a nucleic acid such as an siRNA into an animal-derived cell or organism, being capable of delivering efficiently the nucleic acids into the cells while protecting it from being degraded; and a nucleic acid delivery composition containing the carrier composition and a nucleic acid.

Means for Solving the Problems

The present inventors conducted extensive research to solve the above problems, and found that a composition containing (A) a cationic lipid with a steroid skeleton (steroid nucleus), in combination with (B) a quaternary ammonium salt-type cationic lipid, is useful as a nucleic acid delivery carrier since it has low toxicity and is capable of delivering efficiently the nucleic acids while protecting the nucleic acids from being degraded. The present invention was accomplished by further research based on these findings.

The present invention provides the following items:

Item 1. A carrier composition for delivery of a nucleic acid comprising (A) a cationic lipid with a steroid skeleton (steroid nucleus) and (B) a quaternary ammonium salt-type cationic lipid.

Item 2. A carrier composition according to Item 1, further comprising (C) an oily base material.

Item 3. A carrier composition according to Item 1, wherein component (A) is 3β-[N-(N',N'-dimethylaminoethane)carbamoyl]cholesterol and/or 3β-[N',N',N'-trimethylaminoethane]cholesterol iodide.

Item 4. A carrier composition according to Item 1, wherein component (B) is at least one member selected from the group consisting of dimethyldioctadecylammonium bromide salt, dioleoyltrimethylammonium propane and N-[1-(2,3-bis(oleoyloxy)propyl)-N,N,N-trimethylammonium hydrochloride.

Item 5. A carrier composition according to Item 1, wherein component (B) is contained in a proportion of 10 to 200 parts by weight per 100 parts by weight of component (A).

Item 6. A carrier composition according to Item 1, the carrier composition being a carrier composition for delivery of a siRNA.

Item 7. A nucleic acid delivery composition comprising a carrier composition according to any one of Items 1 to 5 and a nucleic acid.

Item 8. A nucleic acid delivery composition according to Item 7, wherein the nucleic acid is an siRNA.

Item 9. A nucleic acid introduction method comprising bringing a nucleic acid delivery composition according to Item 7 into contact with a cell to introduce the nucleic acid into the cell.

Item 10. Use of (A) a cationic lipid with a steroid skeleton, in combination with (B) a quaternary ammonium salt-type cationic lipid for the production of a carrier composition for delivery of a nucleic acid.

BRIEF DESCRIPTION OF THE DRAWINGS

The patent or application file contains at least one drawing executed in color. Copies of this patent or patent application publication with color drawings will be provided by the Office upon request and payment of the necessary fee.

EFFECTS OF THE INVENTION

Figure 1:
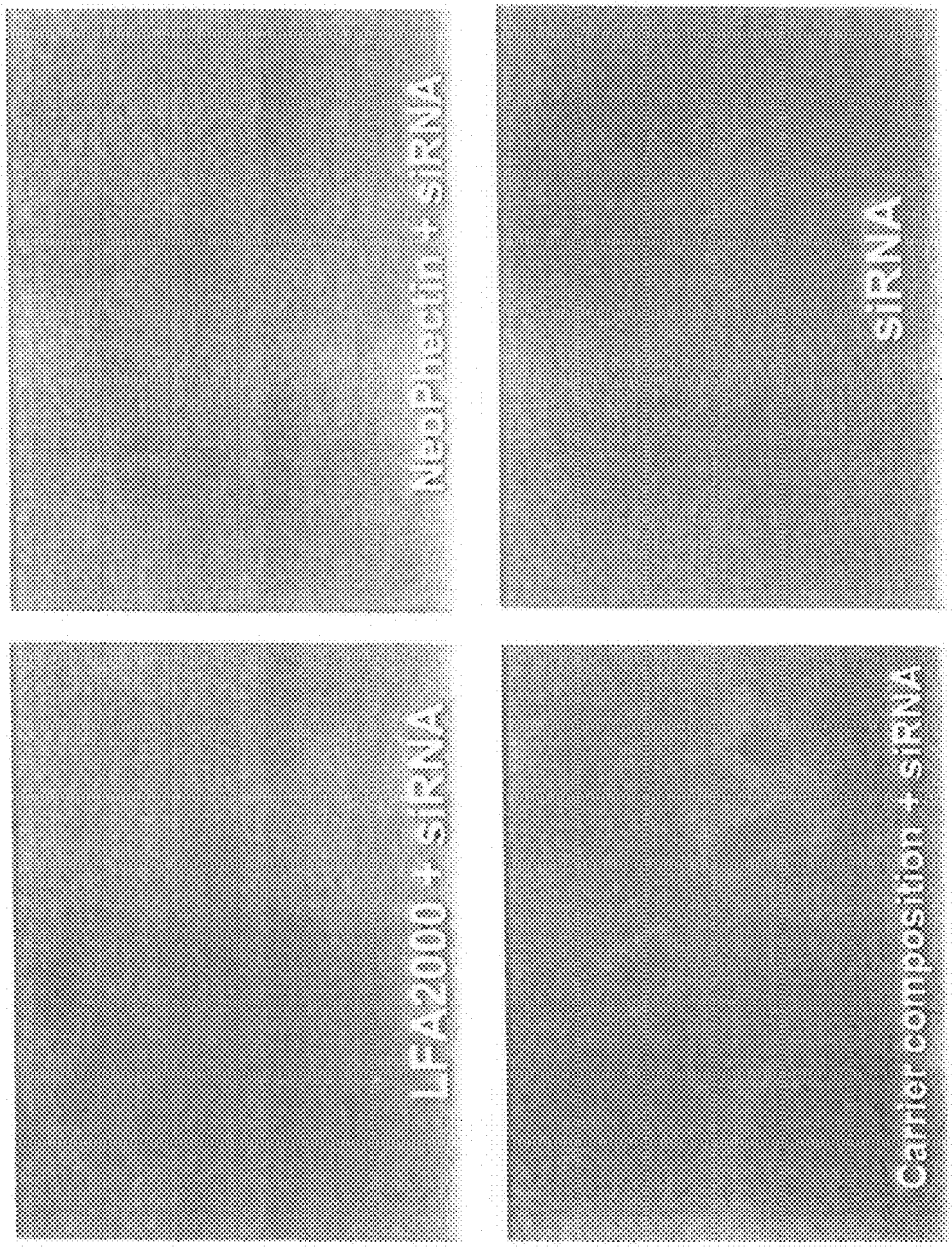
FIG. 1 shows the results of microscopic examination of the fluorescence images derived from the nucleic acid of the cells after treatment using each of the test samples.

The carrier composition for delivery of a nucleic acid and nucleic acid delivery composition of the present invention achieve the following remarkable effects.
(1) Nucleic acids can be efficiently delivered into cells so that they can effectively exhibit their functions in the cells.
(2) Degradation of nucleic acids can be suppressed in organisms and culture media.
(3) The carrier and composition have low toxicity and high safety.

The carrier composition for delivery of a nucleic acid and nucleic acid delivery composition are therefore useful for treating various diseases by nucleic acid introduction, and in particular for treating intractable diseases which are difficult to treat with low molecular weight compounds.

The nucleic acid delivery composition of the present invention is also advantageous in that it can be lyophilized and thus can be stored in a lyophilized state.

BEST MODE FOR CARRYING OUT THE INVENTION

The present invention is described below in detail.
Carrier Composition for Delivery of Nucleic Acid The carrier composition for delivery of a nucleic acid of the present invention comprises (A) a cationic lipid with a steroid skeleton (steroid nucleus) and (B) a quaternary ammonium salt-type cationic lipid.

The carrier composition of the present invention is used as a carrier for delivering (introducing) nucleic acids into cells.

Nucleic acids that can be used with the carrier composition of the present invention are not limited in kind and structure, as long as they are in need of being delivered into cells. Examples of such nucleic acids include siRNAs, mRNAs, tRNAs, rRNAs, cDNAs, miRNAs (microRNAs), ribozymes, antisense oligos, decoy oligonucleotides, plasmid DNAs, peptide nucleic acids, triplex-forming oligonucleotides (TFOs), genes, etc. In particular, the carrier composition of the present invention is useful for the delivery of siRNAs into cells. Nucleic acids to be delivered by the carrier composition of the present invention may be those derived from humans, animals, plants, bacteria, viruses, etc., or those chemically synthesized. Further, such nucleic acids may be single-stranded, double-stranded, or triple-stranded, and are not limited in molecular weight. Further, in the present invention, nucleic acids modified with chemicals, enzymes or peptides are also usable. In the present invention, such nucleic acids can be used singly or in combination.

The cationic lipid with a steroid skeleton (hereinafter sometimes referred to as "component (A)") used in the carrier composition of the present invention is a lipid that is cationic and has a steroid skeleton (perhydrocyclopentaphenanthrene ring; $C_{17}H_{28}$). The cationic lipid with a steroid skeleton for use in the present invention is not limited as long as it is pharmaceutically acceptable. Specific examples of such lipids include 3β-[N-(N',N'-dimethylaminoethane)carbamoyl] cholesterol (DC-Chol), 3β-[N',N',N'-trimethylaminoethane] cholesterol iodide (TC-Chol), bis(guanidinium)-trencholesterol (BGTC), N-cholesteryloxycarbonyl-3,7-diazanonane-1,9-diamine, β-alanine-diethanolamine-cholesterol, $N^4$-spermine cholesteryl carbamate (GL-67), N[$N^4$-3-aminopropylspermidine]cholesteryl carbamate (GL-78), N-spermine cholesteryl carboxyamide (GL-90), $N^1,N^8$-bis(arginic carboxamide)-$N^4$-spermidine cholesteryl carbamate (GL-95), N-[$N^1,N^4,N^8$-tris(3-aminopropyl) spermidine]cholesteryl carbamate (GL-96), and like cholesterol derivatives (cationic lipids with a cholesterol skeleton); squalamine, 3α,7α,12α-tris(3-aminopropoxy)-5β-cholan-24-(N,N-bis(3-aminopropyl)amine), 3α,7α,12α-tris (3-aminopropoxy)-5β-cholan-24-(N-(N-(3-aminopropyl))-3-aminopropyl)amine, 3α,7α,12α-tris(3-azidopropoxy)-5β-cholan-24-(N,N-bis(2-cyanoethyl)amine)), 3α,7α,12α-tris (3-azidopropoxy)-5β-cholan-24-(N-(benzyloxycarbonyl)-N-(3-hydroxypropyl)amine), and like cationic lipids to which steroids are linked; umbrella-spermine conjugates and like cationic lipids to which cholic acid is linked; cationic lipids to which sterol glycoside is linked; cationic lipids to which steroid saponin is linked; etc.

Such cationic simple lipids with a steroid skeleton may be used singly or in combination.

Preferable examples of cationic lipids with a steroid skeleton include cholesterol derivatives (cationic lipids with a cholesterol skeleton), and more preferable examples thereof include 3β-[N—(N',N'-dimethylaminoethane)carbamoyl] cholesterol, and 3β-[N',N',N'-trimethylaminoethane]cholesterol iodide (TC-Chol).

The quaternary ammonium salt-type cationic lipid for use in the present invention (hereinafter sometimes referred to as "component (B)") is not limited as long as it is pharmaceutically acceptable. Specific examples thereof include dimethyldioctadecylammonium bromide (DDAB), 1,2-dimyristoyl-3-trimethylammonium propane, 1,2-dioleoyl-3-trimethylammonium propane (DOTAP), 1,2-dioleoyl-3-trimethylammonium propane methylsulfate, 1,2-dipalmitoyl-3-trimethylammonium propane, 1,2-distearoyl-3-trimethylammonium propane, N-(1-(2,3-bis(oleoyloxy) propyl)-N,N,N-trimethylammonium hydrochloride (DOTMA), dimyristoyloxypropyl dimethylhydroxyethylammonium bromide (DMRIE), dioleoyloxypropyl dimethylhydroxyethylammonium bromide (DORIE), dimethyldidodecylammonium bromide, N-α-trimethylammonioacetyl) didodecyl-D-glutamine hydrochloride, N-α-trimethylammonioacetyl)-O,O'-bis-(1H,1H,2H,2H-perfluorodecyl)-L-glutamine hydrochloride, O,O'-didodecanoyl-N-(α-trimethylammonioacetyl) diethanolamine hydrochloride, methylallyl didodecyl ammonium bromide, N-{p-(ω-trimethylammoniobutyloxy) benzoyl}-didodecyl-L-glutamine hydrochloride, 9-(ω-trimethylammoniobutyl)-3,6-bis(dodecanoyl)carbazole bromide, dimethyldioctadecyl ammonium hydrochloride, N-ω-trimethylammoniodecanoyl-dihexadecyl-D-glutamine bromide, N-{p-(ω-trimethylammoniohexyloxy)-benzoyl}-ditetradecyl-L-glutamine bromide, p-(ω-trimethylammoniodecyloxy)-p'-octyloxyazobenzene bromide salt (MC-1-0810), p-{ω-(β-hydroxyethyl)dimethyl-ammoniodecyloxy}-p'-octyloxyazobenzene bromide salt (MC-3-0810), O,O',O"-tridodecanoyl-N-(ω-trimethyl-ammoniodecanoyl)tris(hydroxymethyl)aminomethane bromide salt (TC-1-12), 1,2-dilauryl-glycero-3-ethylphosphocholine, 1,2-dimyristoyl-glycero-3-ethylphosphocholine, 1,2-dipalmitoyl-glycero-3-ethylphosphocholine, 1,2-distearoyl-glycero-3-ethylphosphocholine, 1,2-dioleoylglycero-3-ethylphosphocholine, 1-palmitoyl-2- oreoyl-glycero-3-ethylphosphocholine, etc. Such quaternary ammonium salt-type cationic lipids may be used singly or in combination.

Among such quaternary ammonium salt-type cationic lipids, preferable are dimethyldioctadecylammonium bromide (DDAB), dioleoyltrimethylammonium propane (DOTAP), N-(1-(2,3-bis(oleoyloxy)propyl)-N,N,N-trimethylammonium hydrochloride (DOTMA), O,O'-didodecanoyl-N-α-trimethylammonioacetyl)diethanolamine hydrochloride (DC-6-12, n=12; and DC-6-14, n=14), p-{ω-(β-hydroxyethyl) dimethylammonio-decyloxy}-p'-octyloxyazobenzene bromide salt (MC-3-0810), and O,O',O"-tridodecanoyl-N-(ω-trimethyl-ammoniodecanoyl)tris(hydroxymethyl)aminomethane bromide (TC-1-12); and particularly preferable are dimethyldioctadecylammonium bromide (DDAB), dioleoyltrimethylammonium propane (DOTAP), and N-(1-(2,3-bis(oleoyloxy)propyl)-N,N,N-trimethylammonium hydrochloride (DOTMA).

In the carrier composition of the present invention, the proportion of component (A) to component (B) is not limited, and from the viewpoint of improved nucleic acid delivery efficiency into cells, the proportion of component (B) may be, for example, 10 to 200 parts by weight, preferably 30 to 150 part by weight, and more preferably 75 to 125 parts by weight, per 100 parts by weight of component (A). The total proportion of components (A) and (B) to the total amount of the carrier composition of the present invention may be, for example, 10 to 100 wt. %, preferably 20 to 80 wt. %, and more preferably 40 to 70 wt. %.

The carrier composition of the present invention may contain an oily base material (hereinafter sometimes referred to as "component (C)"), in addition to components (A) and (B). When an oily base material is added, its properties make it possible to control the efficiency of nucleic acid introduction by the nucleic acid delivery carrier composition. For example, when an oily base material is added to adjust the specific gravity of the carrier composition, the degree of contact of the carrier composition with cells can be controlled to thereby improve introduction efficiency in vitro. Alternatively, for example, when a temperature-sensitive oily base material is added, the core of the carrier composition can be disintegrated under predetermined temperature conditions to induce fluctuations in the cell surface, thereby improving the nucleic acid introduction efficiency. Further alternatively, for example, when an oily base material that has a disruptive ability by external stimulus is added, the core of the carrier composition can be disintegrated by an external stimulus to induce fluctuations in the cell surface, thereby improving the nucleic acid introduction efficiency.

Examples of oily base materials that can be added to the carrier composition of the present invention include perfluorocarbon, perfluoropentane, perfluorooctyl bromide, perfluorohexane, perfluorotributylamine, soybean oil, refined soybean oil, hydrogenated soybean oil, unsaponified soybean oil, squalene, castor oil, clove oil, sorbitan trioleate, turpentine oil, safflower oil, safflower oil fatty acid, oleic acid, palm oil, rapeseed oil, fusel oil, olive oil, linseed oil, sesame oil, chlorophyll oil, croton oil, bergamot oil, cedar oil, orange oil, fennel oil, eucalyptus oil, corn oil, lavender oil, marjoram oil, lemon oil, cotton seed oil, coconut oil, egg yolk oil, rose oil, pine oil, almond oil, peanut oil, camellia oil, camphor white oil, chamomile oil, cinnamon oil, peppermint oil, esterified corn oil, ginger oil, Roman chamomile oil, snake oil, spearmint oil, sunflower seed oil, cacao butter, wheat germ oil, zinc oxide oil, hardened oils, hydrogenated vegetable oils, light liquid paraffin, liquid paraffin, medium chain fatty acid triglycerides, mink oil, bitter orange oil, polyoxyethylene castor oil, polyoxyethylene hydrogenated castor oil 10, polyoxyethylene hydrogenated castor oil 100, polyoxyethylene hydrogenated castor oil 20, polyoxyethylene hydrogenated castor oil 40, polyoxyethylene hydrogenated castor oil 5, polyoxyethylene hydrogenated castor oil 50, polyoxyethylene hydrogenated castor oil 60, polyoxyl 35 castor oil, process oils, etc. Among such oily base materials, perfluoropentane is temperature sensitive, and is characterized by boiling and being gasified at 29.5° C. Further, perfluorohexane, perfluorooctyl bromide and perfluorotributylamine have disruptive ability by external stimulus, and are characterized by causing cavitation in the core of the carrier composition and disintegrating it when receiving an external stimulus such as ultrasonic irradiation.

When an oily base material is contained, the proportion thereof is not limited as long as the effects of the present invention are not impaired, and may be, for example, 0.1 to 50 parts by weight, preferably 1 to 30 parts by weight, and more preferably 5 to 20 parts by weight, per 100 parts by total weight of components (A) and (B).

The nucleic acid delivery carrier of the present invention may further contain a membrane-fusogenic lipid (helper lipid), if necessary. When containing such a membrane-fusible lipid, the carrier composition of the present invention has further improved efficiency of nucleic acid delivery into cells. Examples of such membrane-fusible lipids include dioleoylphosphatidylethanolamine, dioleoylphosphatidylcholine, transphosphatidylphosphatidylethanolamine, 1,2-bis-(10,12-tricosadinoyl)-phosphoethanolamine, 1,2-dielaidoylphosphoethanolamine, 1,2-dihexadecylphosphoethanolamine, 1,2-dihexanoylphosphoethanolamine, 1,2-dilauroylphosphoethanolamine, 1,2-dilinoleoylphosphoethanolamine, 1,2-dimyristoylphosphoethanolamine, 1,2-dioleoylphosphoethanolamine, 1,2-dipalmitoleoylphosphoethanolamine, 1,2-dipalmitoylphosphoethanolamine, 1,2-diphytanoylphosphoethanolamine, 1,2-distearoylphosphoethanolamine, 1-palmitoyl-2-oleoylphosphoethanolamine, 1-palmitoyl-2-(10,12-tricosadinoyl)phosphoethanolamine, 1,2-dioleoylphosphoethanolamine-N-caproylamine, 1,2-dipalmitoylphosphoethanolamine-N-caproylamine, 1,2-dioleoylphosphoethanolamine-N,N-dimethyl, 1,2-dipalmitoylphosphoethanolamine-N,N-dimethyl, 1,2-dipalmitoylphosphoethanolamine-N-dodecanoyl, 1,2-dioleoylphosphoethanolamine-N-dodecanoyl, 1,2-dioleoylphosphoethanolamine-N-dodecanylamine, 1,2-dipalmitoylphosphoethanolamine-N-dodecanylamine, 1,2-dioleoylphosphoethanolamine-N-glutaryl, 1,2-dipalmitoylphosphoethanolamine-N-glutaryl, 1,2-dioleoylphosphoethanolamine-N-lactose, 1,2-dioleoylphosphoethanolamine-N-[4(p-maleimidemethyl) cyclohexane-carboxylate, dipalmitoylphosphoethanolamine-N-[4(p-maleimidemethyl)cyclohexane-carboxylate, 1,2-dipalmitoylphosphoethanolamine-N-[4(p-maleimidephenyl)butylamide, 1,2-dioleoylphosphoethanolamine-N-[4(p-maleimidephenyl) butyrate], 1,2-dioleoylphosphoethanolamine-N-methyl, dipalmitoylphosphoethanolamine-N-methyl, 1,2-dioleoylphosphoethanolamine-N-[3-(2-pyridyldithio)propionate, 1,2-dipalmitoylphosphoethanolamine-N-[3-(2-pyridyldithio)propionate, 1,2-dioleoylphosphoethanolamine-N-(succinyl), 1,2-dipalmitoylphosphoethanolamine-N-(succinyl), etc. Among such lipids, dioleoylphosphatidylethanolamine can be advantageously used in the nucleic acid delivery carrier of the present invention.

When such a membrane fusible lipid is contained, the proportion thereof is not limited as long as the effects of the present invention are not impaired, and may be, for example, 1 to 500 parts by weight, preferably 10 to 250 parts by weight, and more preferably 25 to 100 parts by weight, per 100 parts by total weight of components (A) and (B).

The carrier composition of the present invention may contain various additives such as isotonizing agents, excipients, diluents, thickeners, stabilizers, buffers, preservatives, etc., as required. The amounts of such additives to be added can be suitably selected according to the form of use of the carrier composition.

The carrier composition of the present invention can be produced by mixing components (A) and (B), and optionally other component(s).

Nucleic Acid Delivery Composition

The nucleic acid delivery composition of the present invention comprises the carrier composition described above and a nucleic acid. In this composition, the nucleic acid forms a complex with the component(s) of the carrier composition via ionic and/or hydrophobic bonds, so that the nucleic acid delivery composition has improved nucleic acid delivery into cells.

The nucleic acid delivery composition of the present invention is produced by mixing the carrier composition with a nucleic acid, or by mixing a nucleic acid with the components of the carrier composition in any order.

In the nucleic acid delivery composition of the present invention, the proportion of nucleic acid to the carrier composition varies depending on the types of nucleic acid and nucleic acid delivery carrier, type of cell as nucleic acid delivery target, etc., and the proportion of nucleic acid may be, for example, 0.1 to 300 parts by weight, preferably 1 to 100 parts by weight, and more preferably 2.5 to 50 parts by weight, per 100 parts by total weight of components (A) and (B).

Further, the total amount of components (A) and (B) in the nucleic acid delivery composition may be, for example, 10 to 90 wt. %, preferably 30 to 80 wt. %, and more preferably 50 to 70 wt. %, of the total weight of the composition.

The nucleic acid delivery composition of the present invention may contain various additives such as isotonizing agents, excipients, diluents, thickeners, stabilizers, buffers, preservatives, etc. according to the form of use. The amounts of such additives can be suitably selected according to the form of use of the nucleic acid delivery composition.

In the present invention, examples of cells to which nucleic acids can be delivered include cultured cells, cells isolated from organisms (including established cell lines), cells in vivo, etc.

The form of use of the nucleic acid delivery composition of the present invention is not limited, as long as the composition can be brought into contact with target cells for nucleic acid introduction. When a nucleic acid is delivered into cells in vivo, examples of forms of use of the composition include direct injection into tissue; injection under the skin or into a vein, muscle, abdominal cavity, eye, digestive organ, tooth, etc.; administration by inhalation into the nasal cavity, oral cavity, lungs, etc.; oral administration; transdermal administration; and transmucosal administration through the oral mucosa, vaginal mucosa, ocular mucosa, rectal mucosa or uterine mucosa; and the like. Alternatively, when a nucleic acid is delivered into cultured cells or cells isolated from an organism, the nucleic acid deliver composition can be, for example, previously added to a medium for culturing the cell. A nucleic acid can also be delivered to cultured cells or cells isolated from an organism in the presence of blood serum.

BEST MODE FOR CARRYING OUT THE INVENTION

The present invention is described in detail below with reference to Examples and so forth, which are not intended to limit the scope of the invention.

EXAMPLE 1

A carrier composition for delivery of a nucleic acid having the following formula was prepared.

| | |
|---|---|
| Dimethyldioctadecylammonium bromide | 0.9 μg |
| 3β-[N-(N',N'-dimethylaminoethane)carbamoyl]cholesterol | 0.9 μg |
| Dioleoylphosphatidylethanolamine | 0.9 μg |
| Glycerol | 40.5 μg |
| Purified water | 2 μl |
| OPTI-MEM medium (produced by Invitrongen Corporation) | Appropriate amount |
| Total amount | 50 μl |

EXAMPLE 2

A solution which contains a nucleic acid having the following composition was first prepared.

| | |
|---|---|
| SiRNA | 2 pmol |
| OPTI-MEM medium (produced by Invitrongen Corporation) | Appropriate amount |
| Total amount | 50 μl |

Then, 50 μl of the carrier composition of Example 1 was mixed with 50 μl of the nucleic acid-containing solution, and the mixture was incubated for 20 minutes at room temperature, so as to prepare a nucleic acid delivery composition.

EXAMPLE 3

A carrier composition for delivery of a nucleic acid having the following formula was prepared.

| | |
|---|---|
| Dimethyldioctadecylammonium bromide | 0.5 mg |
| 3β-[N-(N',N'-dimethylaminoethane)carbamoyl]cholesterol | 0.5 mg |
| Dioleoylphosphatidylethanolamine | 0.5 mg |
| Sucrose | 88.9 mg |
| Purified water | Appropriate amount |
| Total amount | 1.0 ml |

EXAMPLE 4

A carrier composition for delivery of a nucleic acid having the following formula was prepared.

| | |
|---|---|
| Dimethyldioctadecylammonium bromide | 0.5 mg |
| 3β-[N-(N',N'-dimethylaminoethane)carbamoyl]cholesterol | 0.5 mg |

-continued

| | |
|---|---|
| Dioleoylphosphatidylethanolamine | 0.5 mg |
| Purified water | Appropriate amount |
| Total amount | 1.0 ml |

TEST EXAMPLE 1

In order to evaluate the ability of the nucleic acid delivery composition of Example 2 to deliver siRNA into cells, the following tests were performed using A549 cells (cell strain derived from human lung cancer; Dainippon Pharmaceutical Co. Ltd.) as model cells. In this test, fluorescently-labeled GL3-siRNA (siRNA targeting firefly luciferase; Dharmacon Corporation, Boulder, Colo., USA; Sense: 5'-CUUACGCUGAGUACUUCGAdTdT; Antisense: 5'-UCGAAGUACUCAGCGUAAGdTdT) was used.

Firstly, A549 cells, whose concentration had been adjusted to $1.2 \times 10^5$ cells/ml with DMEM medium (Dulbecco-Minimum Essential Medium), were seeded in a 24-well plate at $6.0 \times 10^4$ cells per well. Next, 500 µl of one of each of the test samples shown in Table 1 was added to each well, and incubated at 37° C. in 5% $CO_2$ for 24 hours. Fluorescence images derived from the nucleic acid in the cells were observed with a fluorescence microscope (Olympus IX 71 fluorescence microscope; Olympus, Tokyo, Japan), so as to evaluate the ability of each test sample to deliver siRNA into cells.

TABLE 1

| | Test sample | |
|---|---|---|
| No | Indication in FIG. 1 | Formula |
| 1 | Carrier composition + siRNA | The nucleic acid delivery composition of Example 2 |
| 2 | LFA2000 + siRNA | OPTI-MEM medium containing LFA2000(Lipofectamine2000; Prpduced by Invitrogen Corporation)(1.0 mg/mL), and siRNA (20 pmol/ml) |
| 3 | NeoPhectin + siRNA | OPTI-MEM medium containing NeoPhectin (Prpduced by NeoPharm) (1.0 mg/mL), and siRNA (20 pmol/ml) |
| 4 | siRNA | OPTI-MEM medium containing siRNA (20 pmol/ml) |

The results are shown in FIG. 1. When only the siRNA was added, no fluorescence was observed in the cells. In contrast, when the nucleic acid delivery composition of Example 2 or a known cell delivery carrier (i.e., LFA 2000 or NeoPhectin) was added together with the siRNA, fluorescence was observed in the cells. Particularly when the nucleic acid delivery composition of Example 2 was used, strong fluorescence was observed in the cells. These results confirmed that the nucleic acid delivery composition of the invention exhibits an excellent nucleic acid delivery ability.

TEST EXAMPLE 2

In order to evaluate the suppression of a target gene at the protein level, a plasmid coding for the luciferase gene was temporarily introduced into cells, and subsequently the nucleic acid delivery composition of Example 2 was added to the cells, so as to evaluate the amount of luciferase expression. In the test, GL3-siRNA (siRNA targeting firefly luciferase; Dharmacon Corporation, Boulder, Colo., USA; sense: 5'-CUUACGCUGAGUACUUCGAdTdT (SEQ ID NO: 1); antisense: 5'-UCGAAGUACUCAGCGUAAGdTdT (SEQ ID NO: 2)) was used.

More specifically, 10 µg of pGL3 Luciferase or Renilla Luciferase (Promega, Madison, Wis., USA) was added to $5 \times 10^6$ A549 cells (cell strain derived from human lung cancer; produced by Dainippon Pharmaceutical Co. Ltd.), and the cells were electroporated using a nucleofector (Amaxa Inc., Gaithersburg, Md., USA). The cells having introduced pGL3 Luciferase and Renilla Luciferase therein were adjusted to $1.2 \times 10^5$/ml with DMEM medium (Dulbecco-Minimum Essential Medium), which is serum-free or contains 10% by volume of fetal bovine serum, and were subsequently seeded in a 24-well plate at $6.0 \times 10^4$ cells per well. Then, 500 µl of one of each of the test samples shown in Table 2 was added to each well, and incubated at 37° C. in 5% $CO_2$ for 24 hours. The cells in the wells were lysed by a conventional process to prepare cell lysates, and the cell lysates were evaluated for luciferase activity using a Dual-Luciferase Reporter Assay System (Promega, Madison, Wis., USA). Luciferase activities were evaluated by calculating the ratio of the firefly luciferase to the Renilla Luciferase activities (relative activity: %).

TABLE 2

Figure 2:
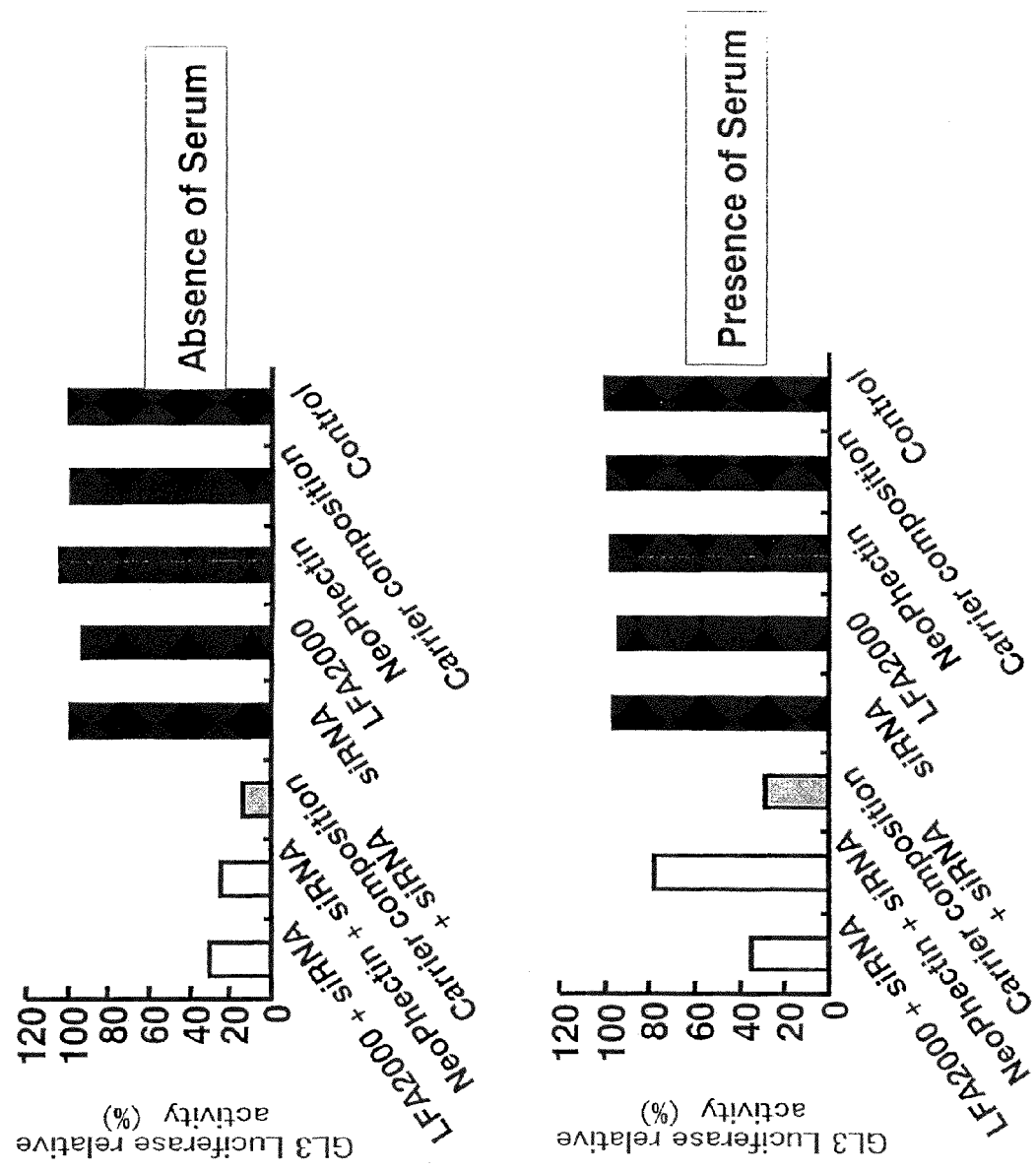
FIG. 2 shows charts illustrating the results of measurement of the luciferase activities of the cells after treatment using each of the test samples.

| | Test sample | |
|---|---|---|
| No | Indication in FIG. 2 | Formula |
| 1 | Carrier composition + siRNA | The nucleic acid delivery composition of Example 2 |
| 2 | LFA2000 + siRNA | OPTI-MEM medium containing LFA2000(Lipofectamine2000; Prpduced by Invitrogen Corporation)(1.0 mg/mL), and siRNA (20 pmol/ml) |
| 3 | NeoPhectin + siRNA | OPTI-MEM medium containing NeoPhectin (Prpduced by NeoPharm) (1.0 mg/mL), and siRNA (20 pmol/ml) |
| 4 | SiRNA | OPTI-MEM medium containing siRNA (20 pmol/ml) |

TABLE 2-continued

| No | Indication in FIG. 2 | Formula |
|---|---|---|
| 5 | LFA2000 | OPTI-MEM medium containing LFA2000(Lipofectamine2000; Prpduced by Invitrogen Corporation)(1.0 mg/mL) |
| 6 | NeoPhectin | OPTI-MEM medium containing NeoPhectin (Prpduced by NeoPharm)(1.0 mg/mL) |
| 7 | carrier composition | OPTI-MEM medium containing the carrier composition of Example 1(50% by volume) |
| 8 | Control | OPTI-MEM medium |

The results are shown in Table 2. The results confirmed that the use of the nucleic delivery composition of Example 2 enables highly effective siRNA delivery into cells and expression of the siRNA function in the cells, regardless of the presence or absence of serum in the medium.

TEST EXAMPLE 3

In this test, the carrier composition of Example 3 was evaluated for its ability to deliver siRNA into lung tissue cells and for the siRNA functionality in the cells, using Rat neprilysin (siRNA targeting Rat neprilysin (NM_012608); RNA-TEC NV Corporation, Belgium; Sense: 5'-GCUCCAAAGC-CGAAGAAGAdTdT (SEQ ID NO: 3), Antisense: 5'-UCUUCUUCGGCUUUGGAGCdTdT(SEQ ID NO: 4)).

The nucleic acid delivery composition was prepared by mixing the carrier composition of Example 3 with siRNA at a ratio 1:1 by weight. Then, 0.4 ml of a test solution, which was prepared by diluting the nucleic acid delivery composition with an appropriate carrier (8.89 w/v% sucrose solution), was administered via the lungs to male SD rats weighing 250-320 g while being anesthetized with an inhalation anesthetic agent, isoflurane (produced by Dainippon Pharmaceutical Co., Ltd.), using an IA-1B Inhalation Device (PENNCENTURY, Philadelphia, Pa., USA). The test solution was prepared by diluting the nucleic acid delivery composition as appropriate so that the siRNA dose was 0.04 to 1.2 mg/kg (per rat). Twenty-four hours after the pulmonary administration, each rat was anesthetized with ether, and was fixed in the supine position. A midline abdominal incision was made, and the rat was killed by exsanguination via the abdominal inferior vena cava. The lungs were subsequently removed from the rat, and were washed with physiological saline cooled with ice. Using the removed lungs, the amount of mRNA expression of a model target gene, NEP (neutral endopeptidase), and the amount of mRNA expression of a housekeeping gene, GAPDH (glyceraldehyde-3-phosphate dehydrogenase), were measured. Moreover, the Rat Neprilysin (NEP) activity in the removed lungs was measured. The measurement methods and results are described in detail below. As a control, a test was similarly performed by administering only the carrier (8.89 w/v% sucrose solution)to rats under the same conditions. For comparison, a test was also performed using siRNA (Takara, Japan; Sense: 5'-GAACGGCAUCAAG-GUGAACTT (SEQ ID NO: 5), Antisense: 5'-GUUCACCU-UGAUGCCGUUCTT (SEQ ID NO: 6)) targeting EGFP (enhanced green fluorescent protein) instead of Rat Neprilysin.
<Method and Results of Quantifying NEP mRNA and GAPDH mRNA>

Total RNA was isolated from a portion of the removed lungs, and was purified, using an RNeasy Mini Kit (QIAGEN, Germany). The conversion of the mRNAs to cDNAs was performed using a SuperScript III First-Strand Synthesis System for RT-PCR (Invitrogen, California, USA). The amount of the mRNA for the model target gene NEP (neutral endopeptidase) was quantified by real-time PCR, using the prepared cDNA. Similarly, the amount of the mRNA for the housekeeping gene GAPDH (glyceraldehyde-3-phosphate dehydrogenase) was quantified. The suppression of Neprilysin mRNA expression was evaluated by calculating the ratio of NEP mRNA to GAPDH mRNA.

The result confirmed that Neprilysin mRNA expression in the lungs was significantly supressed by Neprilysin-siRNA at a dose of 0.08 mg/kg. Because this dose is lower than those previously reported as providing in vivo RNAi effects, it was demonstrated that effective siRNA delivery into lung tissue cells can be achieved by using the carrier composition of Example 3.
<Method and Results of Measuring Rat Neprilysin (NEP) Activity>

A portion of the removed lungs was homogenized, and the Rat neprilysin activity in the homogenate was measured. The Rat neprilysin (NEP) activity was determined by measuring how much the NEP substrate, DAGNPG (N-Dansyl-D-Ala-Gly-p-nitro-Phe-Gly: SIGMA), was hydrolyzed in a given period in the presence or absence of an NEP specific inhibitor, phosphoramidon (SIGMA), and evaluating the difference in the amounts of hydrolysate in the presence or absence of the inhibitor. The rat lung homogenate was used in an amount of 50 μl; the substrate DAGPNG was used in a concentration of 1 mM; and the inhibitor, phosphoramidon, where present, was added to a concentration of 10 mM, so that the reactions were carried out in a total volume of 100 μl. The reactions were carried out at 37° C. for 10 minutes, and were stopped by incubating at 90° C. for 10 minutes. The NEP activity was determined by measuring the amounts of the resulting hydrolysate DAG (Dansyl-D-Ala-Gly). The amount of hydrolysate produced was determined by measuring fluorescence of the hydrolysate: excitation was performed at 360 nm, and fluorescence emission at 535 nm was measured.

Figure 3:
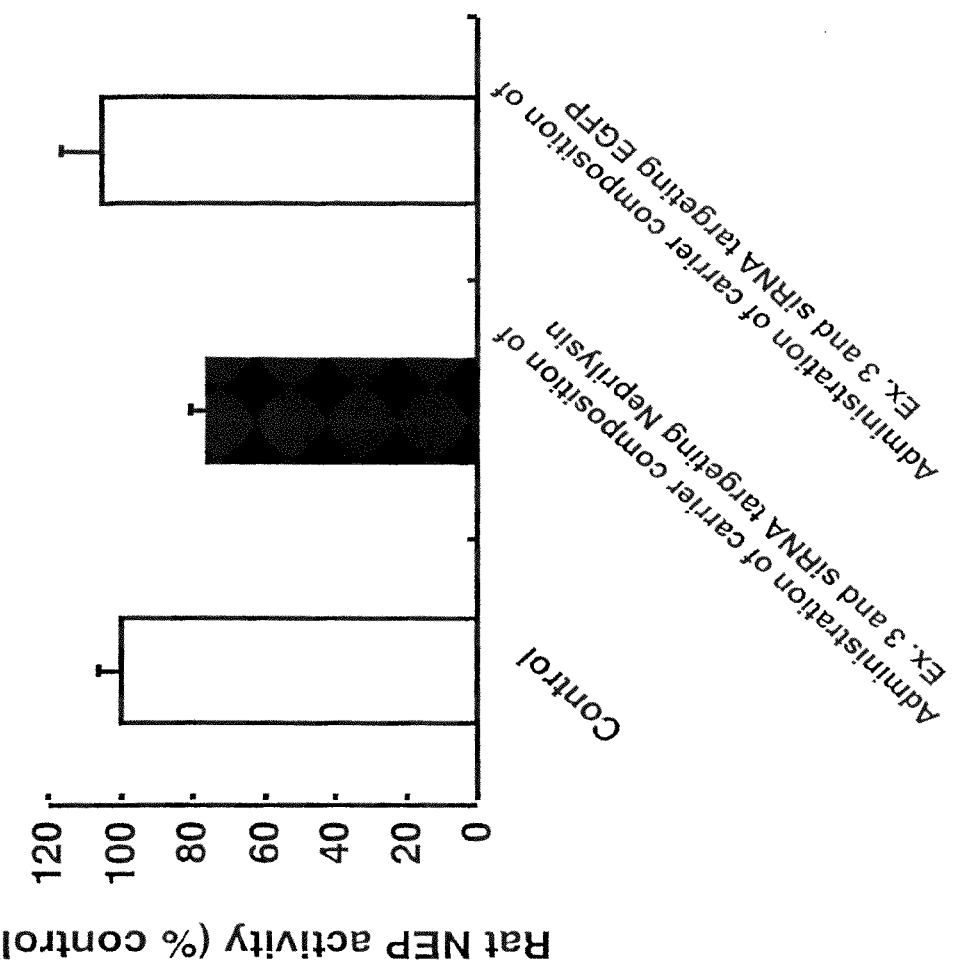
FIG. 3 shows the results of measurement of neprilysin (NEP) activities in the lungs of rats.

The results in the case of siRNA dose of 0.4 mg/kg are shown in FIG. 3. The results show that NEP activity in the lungs was significantly suppressed by NF-siRNA at a dose of 0.4 mg/kg. Accordingly, the aforementioned results also confirmed that effective siRNA delivery into lung tissue cells can be achieved by using the carrier composition of Example 3.

TEST EXAMPLE 4

The carrier composition of Example 1 was evaluated for cytotoxicity using a Premix WST-1 Cell Proliferation Assay System (Takara, Siga, Japan). More specifically, A549 cells (cell strain derived from human lung cancer; produced by Dainippon Pharmaceutical Co. Ltd.), whose concentration had been adjusted to $1 \times 10^5$ cells/ml with DMEM medium (Dulbecco-Minimum Essential Medium), were seeded in a 96-well plate at $10^4$ cells per well. One of each of the test samples, i.e., carrier composition of Example 1, LFA2000

(Lipofectamine 2000; produced by Invitrogen) and NeoPhectin (produced by NeoPharm Corporation), were subsequently added into each well at a concentration of 2 to 20 μg/ml. Then, 10 μl of a Premix WST-1 solution was added into each well, and the cells were incubated at 37° C. for 1 hour. The absorbance of each well at 450 nm was subsequently measured using a microplate reader (Tecan, Maennedorf, Switzerland). As a control, a medium was added to wells instead of the test samples, and measurement was similarly performed. The absorbance at 450 nm represents the absorbance of the formazan dye which is formed from the WST-1 by a reductase. Because there is a linear relationship between this absorbance and living cells, a calibration curve between the number of seeded living cells and absorbance was prepared. The number of the cells of each test sample was determined based on the calibration curve.

Figure 4:
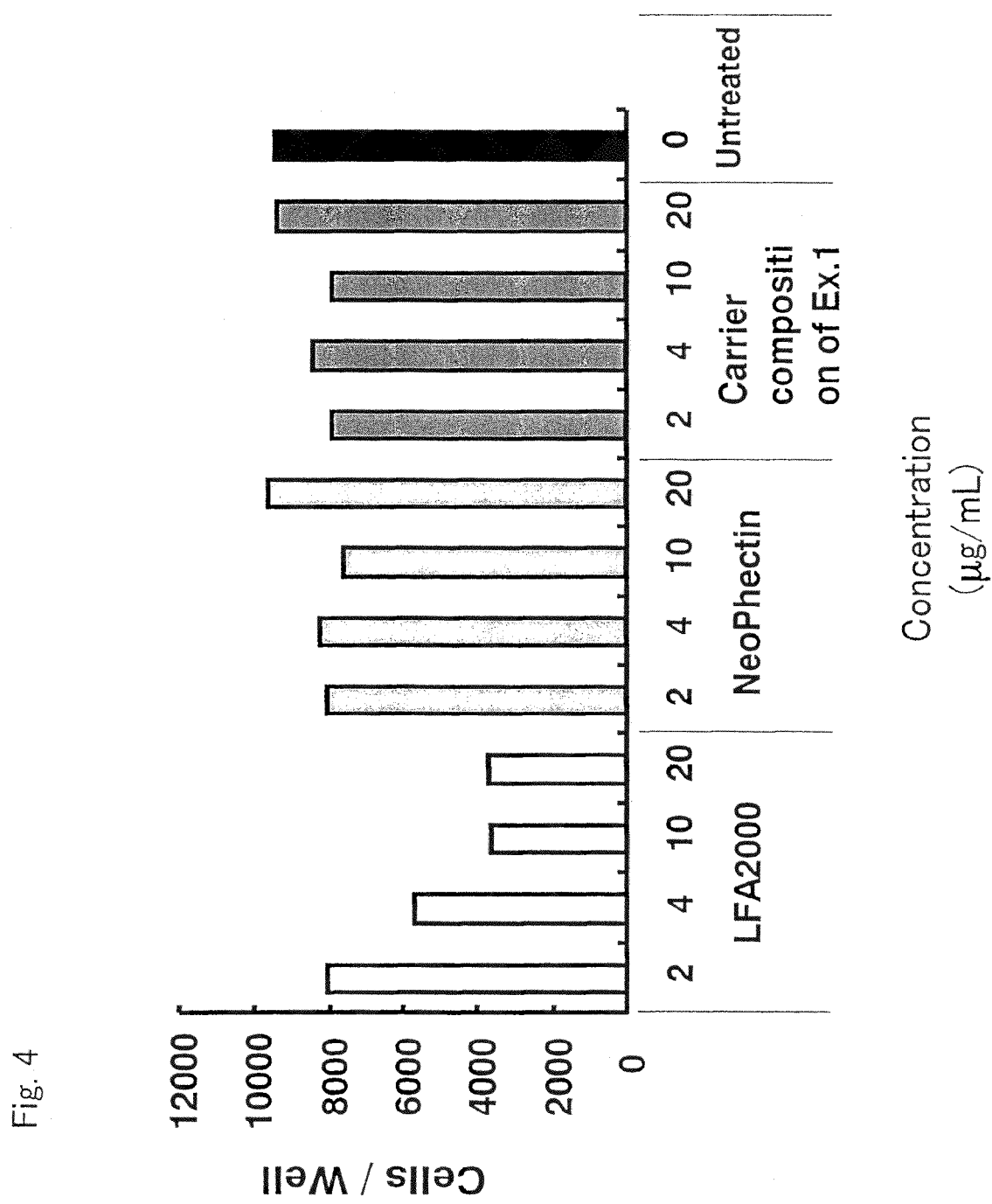
FIG. 4 shows the results of measurement of the number of living cells after treatment using each of the test samples.

The results are shown in FIG. 4. The results confirmed that the number of cells hardly decreased with the addition of the carrier composition of Example 1, and hence the carrier composition has low toxicity and is highly safe.

TEST EXAMPLE 5

To male SD rats (SLC, Tokyo, Japan) weighing 250-320 g were administered via the lungs a test solution prepared by diluting 500 μg of the carrier composition of Example 4 with purified water to 0.4 ml using a 1A-IC device produced by Penncentury Corporation. Each rat after administration was returned to the cage, and kept under normal conditions. Twenty-four hours after the pulmonary administration, 50 mg/kg (1 ml/kg) of pentobarbital (Nembutal, produced by Dainippon Pharmaceutical Co. Ltd.) was intraperitoneally administered to the rat, and the rat under anesthesia was subsequently fixed in the supine position. A midline abdominal incision was made, the rat was killed by exsanguination via the abdominal inferior vena cava. The lungs were subsequently removed from the rat, and were washed with physiological saline cooled with ice. Slices of the removed lung tissue were prepared, and the slices were examined microscopically by staining with hematoxylin and eosin, so as to evaluate the toxicity of the carrier composition to lung tissue. For comparison, tests were performed under the same conditions as above, using LFA2000 (Lipofectamine 2000; produced by Invitrogen) or NeoPhectin (produced by NeoPharm Corporation) instead of the carrier composition of Example 4. Because rats were killed by administration of 500 μg of LFA2000, the test was performed with the dose of LFA2000 changed to 250 μg.

Figure 5:
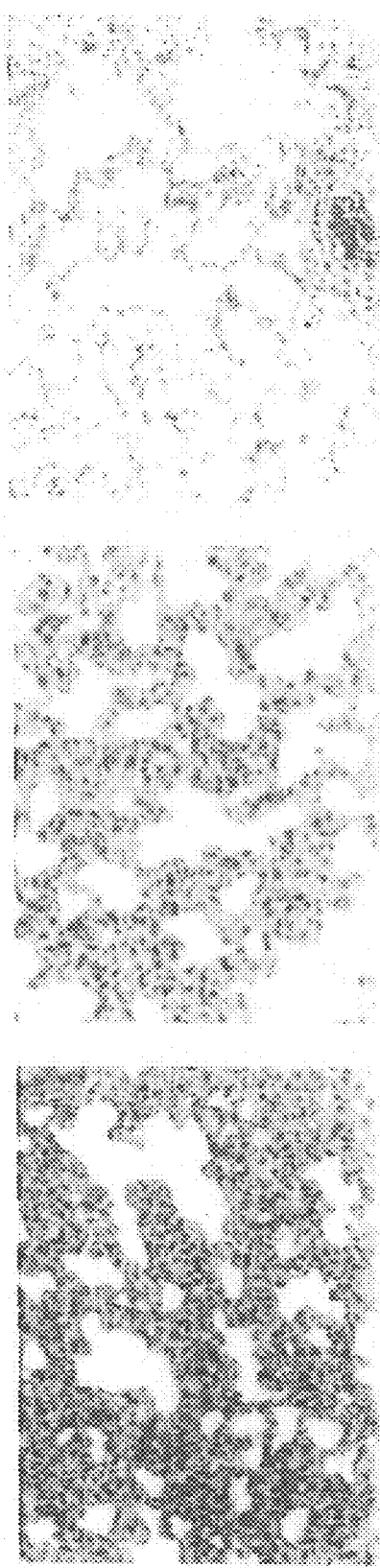
FIG. 5 shows the results of staining slices of lung tissues of rats with hematoxylin and eosin, in which the nuclei, ribosomes, etc. are stained blue to azure with hematoxylin, and the cytoplasm, fibers, and red blood cells are stained red with eosin.

The results are shown in FIG. 5. Inflammation occurred in the rats to which LFA2000 and NeoPhectin were locally administered to the lungs, and local edemata were observed. In contrast, it was confirmed that such inflammation symptoms were reduced in the rats to which the carrier composition of Example 4 had been administered. The results confirmed that the carrier composition of Example 4 has low toxicity even after local pulmonary administration, and is highly safe.

The invention claimed is:

1. A carrier composition for delivery of a nucleic acid consisting essentially of a cationic lipid with a steroid skeleton, a cationic lipid with a quaternary ammonium and a helper lipid; wherein the nucleic acid is an siRNA.

2. A carrier composition for delivery of a nucleic acid consisting essentially of a cationic lipid with a steroid skeleton, a cationic lipid with a quaternary ammonium, an oily base material and a helper lipid.

3. A carrier composition according to claim 1, wherein the cationic lipid with a steroid skeleton is 3β-[N-(N',N'-dimethylaminoethane)carbamoyl]cholesterol and/or 3β-[N',N',N'-trimethylaminoethane]cholesterol iodide.

4. A carrier composition according to claim 1, wherein the cationic lipid with a quaternary ammonium is at least one member selected from the group consisting of dimethyldioctadecylammonium bromide salt, dioleoyltrimethylammonium propane and N-[1-(2,3-bis(oleoyloxy)propyl)-N,N,N-trimethylammonium hydrochloride.

5. A carrier composition according to claim 1, wherein the cationic lipid with a quaternary ammonium is contained in a proportion of 10 to 200 parts by weight per 100 parts by weight of the cationic lipid with a steroid skeleton.

6. A nucleic acid delivery composition comprising a carrier composition according to claim 1 and a nucleic acid.

7. A method of delivering a nucleic acid comprising bringing the nucleic acid delivery composition according to claim 6 into contact with a cell to introduce the nucleic acid into the cell.

8. A method of preparing a carrier composition for delivery of a nucleic acid consisting essentially of combining a cationic lipid with a steroid skeleton, -a cationic lipid with a quaternary ammonium with a helper lipid to produce a carrier composition for delivery of a nucleic acid; wherein the nucleic acid is an siRNA.

9. A carrier composition according to claim 1, wherein the helper lipid is at least one member selected from the group consisting of dioleoylphosphatidylethanolamine, dioleoylphosphatidylcholine, and transphosphatidylphosphatidylethanolamine.

10. A carrier composition according to claim 2, wherein the cationic lipid with a steroid skeleton is 3β-[N-(N',N'-dimethylaminoethane)carbamoyl]cholesterol and/or 3β-[N',N',N'-trimethylaminoethane]cholesterol iodide.

11. A carrier composition according to claim 2, wherein the cationic lipid with a quaternary ammonium is at least one member selected from the group consisting of dimethyldioctadecylammonium bromide salt, dioleoyltrimethylammonium propane and N-[1-(2,3-bis(oleoyloxy)propyl)-N,N,N-trimethylammonium hydrochloride.

12. A carrier composition according to claim 2, wherein the cationic lipid with a quaternary ammonium is contained in a proportion of 10 to 200 parts by weight per 100 parts by weight of the cationic lipid with a steroid skeleton.

13. A nucleic acid delivery composition comprising a carrier composition according to claim 2 and a nucleic acid.

14. A nucleic acid delivery composition according to claim 13, wherein the nucleic acid is an siRNA.

15. A carrier composition according to claim 2, wherein the helper lipid is at least one member selected from the group consisting of dioleoylphosphatidylethanolamine, dioleoylphosphatidylcholine, and transphosphatidylphosphatidylethanolamine.

16. A method of delivering a nucleic acid comprising bringing the nucleic acid delivery composition according to claim 13 into contact with a cell to introduce the nucleic acid into the cell.

17. A method of preparing a carrier composition for delivery of a nucleic acid consisting essentially of combining a cationic lipid with a steroid skeleton, a cationic lipid with a quaternary ammonium, and an oily base material with a helper lipid to produce a carrier composition for delivery of a nucleic acid; wherein the nucleic acid is an siRNA.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: sense

<400> SEQUENCE: 1
cuuacgcuga guacuucgat t                                            21

<210> SEQ ID NO 2
<211> LENGTH: 21
<212> TYPE: DNA
<213> ORGANISM: Artificial Sequence
<220> FEATURE:
<223> OTHER INFORMATION: antisense

<400> SEQUENCE: 2
ucgaaguacu cagcguaagt t                                            21

<210> SEQ ID NO 3
<211> LENGTH: 21
<212> TYPE: DNA
<213> ORGANISM: Artificial Sequence
<220> FEATURE:
<223> OTHER INFORMATION: sense

<400> SEQUENCE: 3
gcuccaaagc cgaagaagat t                                            21

<210> SEQ ID NO 4
<211> LENGTH: 21
<212> TYPE: DNA
```

```
<213> ORGANISM: Artificial Sequence
<220> FEATURE:
<223> OTHER INFORMATION: antisense

<400> SEQUENCE: 4
ucuucuucgg cuuuggagct t                                              21

<210> SEQ ID NO 5
<211> LENGTH: 21
<212> TYPE: DNA
<213> ORGANISM: Artificial Sequence
<220> FEATURE:
<223> OTHER INFORMATION: sense

<400> SEQUENCE: 5
gaacggcauc aaggugaact t                                              21

<210> SEQ ID NO 6
<211> LENGTH: 21
<212> TYPE: DNA
<213> ORGANISM: Artificial Sequence
<220> FEATURE:
<223> OTHER INFORMATION: antisense

<400> SEQUENCE: 6
guucaccuug augccguuct t                                              21
```